US010271839B2

(12) United States Patent
Mayer et al.

(10) Patent No.: US 10,271,839 B2
(45) Date of Patent: Apr. 30, 2019

(54) METHOD AND IMPLANT FOR STABILIZING SEPARATED BONE PORTIONS RELATIVE TO EACH OTHER

(71) Applicant: Woodwelding AG, Stansstad (CH)

(72) Inventors: Jörg Mayer, Niederlenz (CH); Andreas Wenger, Muri b. Bern (CH)

(73) Assignee: WOODWELDING AG, Stansstad (CH)

( * ) Notice: Subject to any disclaimer, the term of this patent is extended or adjusted under 35 U.S.C. 154(b) by 0 days.

(21) Appl. No.: 15/950,503

(22) Filed: Apr. 11, 2018

(65) Prior Publication Data
US 2018/0228489 A1 Aug. 16, 2018

Related U.S. Application Data

(62) Division of application No. 14/233,062, filed as application No. PCT/CH2012/000157 on Jul. 10, 2012, now Pat. No. 9,955,964.
(Continued)

(51) Int. Cl.
*A61B 17/06* (2006.01)
*A61B 17/064* (2006.01)
(Continued)

(52) U.S. Cl.
CPC .......... *A61B 17/0642* (2013.01); *A61B 17/68* (2013.01); *A61B 17/84* (2013.01);
(Continued)

(58) Field of Classification Search
CPC .............. A61B 17/064; A61B 17/0642; A61B 17/0643; A61B 17/0644; A61B 17/68;
(Continued)

(56) References Cited

U.S. PATENT DOCUMENTS 3,918,442 A * 11/1975 Nikolaev ............... A61B 17/00
606/53
4,548,202 A * 10/1985 Duncan .............. A61B 17/0643
606/220

(Continued)

FOREIGN PATENT DOCUMENTS

EP 2596764 5/2013
WO 2008/088777 7/2008
(Continued)

*Primary Examiner* — Eric S Gibson
(74) *Attorney, Agent, or Firm* — Rankin, Hill & Clark LLP

(57) ABSTRACT

An implant for stabilizing two separated bone portions relative to each other an implant includes a peg, a bridge assembly and a securing element. The peg and bridge assembly include at least two peg portions and a bridge portion, wherein the bridge portion is arranged between the peg portions and wherein the peg and bridge portions are rigidly connected. The peg and bridge assembly is positioned relative to the bone portions such that one peg portion extends into the bone tissue of each one of the bone portions and the bridge portion extends across the gap separating the bone portions. The securing element is anchored in the bone tissue of one of the bone portions, its proximal end extending through an opening in an assembly portion extending parallel to a bone surface or across a notch in a proximal edge of an assembly portion.

21 Claims, 9 Drawing Sheets

Related U.S. Application Data

(60) Provisional application No. 61/508,801, filed on Jul. 18, 2011.

(51) Int. Cl.
*A61B 17/68* (2006.01)
*A61B 17/84* (2006.01)
*A61B 17/00* (2006.01)

(52) U.S. Cl.
CPC ............... *A61B 2017/00955* (2013.01); *A61B 2017/0641* (2013.01)

(58) Field of Classification Search
CPC ..... A61B 17/80–17/8095; A61B 17/84; A61B 17/844; A61B 17/846; A61B 17/848; A61B 2017/0641; A61B 2017/0645; A61B 2017/0646; A61B 2017/0647; A61B 2017/0649
USPC ........................................... 606/75; 227/902
See application file for complete search history.

(56) References Cited

U.S. PATENT DOCUMENTS

| | | | | |
|---|---|---|---|---|
| 4,573,469 A * | 3/1986 | Golden | A61B 17/068 | 411/363 |
| 5,084,050 A * | 1/1992 | Draenert | A61F 2/30767 | 606/304 |
| 5,120,175 A * | 6/1992 | Arbegast | F16B 1/0014 | 29/447 |
| 5,290,281 A * | 3/1994 | Tschakaloff | A61B 17/8085 | 219/229 |
| 5,380,221 A * | 1/1995 | Grabbe | H05K 3/303 | 411/909 |
| 5,780,536 A * | 7/1998 | Yokoyama | B29C 65/1425 | 411/390 |
| 6,045,552 A * | 4/2000 | Zucherman | A61B 17/1604 | 606/71 |
| 6,080,161 A * | 6/2000 | Eaves, III | A61B 17/68 | 606/329 |
| 6,228,085 B1 * | 5/2001 | Theken | A61B 17/7059 | 606/289 |
| 6,332,885 B1 * | 12/2001 | Martella | A61B 17/68 | 606/286 |
| 6,913,666 B1 * | 7/2005 | Aeschlimann | B29C 65/56 | 156/303.1 |
| 6,921,264 B2 * | 7/2005 | Mayer | A61B 17/68 | 433/173 |
| 7,008,226 B2 * | 3/2006 | Mayer | A61B 17/68 | 433/173 |
| 7,108,697 B2 * | 9/2006 | Mingozzi | A61B 17/8095 | 606/286 |
| 7,160,405 B2 * | 1/2007 | Aeschlimann | B29C 65/08 | 156/298 |
| 7,335,205 B2 * | 2/2008 | Aeschlimann | A61B 17/00491 | 606/232 |
| 7,967,820 B2 * | 6/2011 | Bonutti | A61B 17/0401 | 606/64 |
| 8,225,479 B2 * | 7/2012 | Clinch | B29C 66/43421 | 29/525.05 |
| 8,357,201 B2 * | 1/2013 | Mayer | A61F 2/30 | 623/18.11 |
| 8,496,657 B2 * | 7/2013 | Bonutti | A61B 17/0401 | 606/62 |
| 8,518,314 B2 * | 8/2013 | Lehmann | B29C 65/562 | 264/248 |
| 8,528,299 B2 * | 9/2013 | Cove | B29C 65/08 | 52/376 |
| 8,545,536 B2 * | 10/2013 | Mayer | A61B 17/0401 | 606/232 |
| 8,777,618 B2 * | 7/2014 | Baehre | A61B 17/00491 | 433/201.1 |
| 8,845,699 B2 * | 9/2014 | Bonutti | A61B 17/0401 | 606/300 |
| 8,870,572 B2 * | 10/2014 | Mayer | A61B 17/68 | 433/173 |
| 8,911,234 B2 * | 12/2014 | Mayer | A61B 17/68 | 433/173 |
| 8,950,159 B2 * | 2/2015 | Cove | B29C 65/08 | 52/376 |
| 8,951,254 B2 * | 2/2015 | Mayer | A61B 17/1682 | 606/75 |
| 9,017,380 B2 * | 4/2015 | Mayer | A61B 17/0469 | 606/151 |
| 9,023,088 B2 * | 5/2015 | Voisard | A61B 17/0401 | 606/313 |
| 9,072,554 B2 * | 7/2015 | Reynolds | A61B 17/7059 | |
| 9,220,609 B2 * | 12/2015 | Mueller | A61B 17/7059 | |
| 9,226,784 B2 * | 1/2016 | Lehmann | A61B 17/0401 | |
| 9,241,740 B2 * | 1/2016 | Mayer | A61B 17/0642 | |
| 9,289,301 B2 * | 3/2016 | Mayer | A61F 2/30 | |
| 9,345,493 B2 * | 5/2016 | Nakaji | A61B 17/1695 | |
| 9,357,996 B2 * | 6/2016 | Voisard | A61B 17/0401 | |
| 9,386,976 B2 * | 7/2016 | Mayer | A61B 17/0401 | |
| 9,955,964 B2 * | 5/2018 | Mayer | A61B 17/0642 | |
| 2002/0143329 A1 | 10/2002 | Serhan | A61B 17/0642 | 623/13.11 |
| 2004/0030341 A1 * | 2/2004 | Aeschlimann | A61B 17/00491 | 606/232 |
| 2004/0038180 A1 * | 2/2004 | Mayer | A61B 17/68 | 433/173 |
| 2004/0053196 A1 * | 3/2004 | Mayer | A61B 17/68 | 433/173 |
| 2005/0049600 A1 * | 3/2005 | Groiso | A61B 17/0642 | 606/75 |
| 2005/0080454 A1 * | 4/2005 | Drews | A61B 17/064 | 606/221 |
| 2005/0165394 A1 * | 7/2005 | Boyce | A61B 17/68 | 606/54 |
| 2005/0251147 A1 | 11/2005 | Novak | | |
| 2006/0058802 A1 * | 3/2006 | Kofoed | A61B 17/0642 | 606/75 |
| 2006/0105295 A1 | 5/2006 | Mayer | | |
| 2006/0111782 A1 * | 5/2006 | Petersen | A61B 17/1604 | 623/17.11 |
| 2006/0167459 A1 * | 7/2006 | Groiso | A61B 17/0642 | 606/248 |
| 2006/0241609 A1 * | 10/2006 | Myerson | A61B 17/562 | 606/281 |
| 2007/0265622 A1 * | 11/2007 | Aeschlimann | A61B 17/00491 | 606/60 |
| 2007/0265704 A1 * | 11/2007 | Mayer | A61B 17/0469 | 623/11.11 |
| 2007/0270833 A1 * | 11/2007 | Bonutti | A61B 17/0401 | 606/28 |
| 2007/0276388 A1 * | 11/2007 | Robertson | A61B 17/0057 | 606/75 |
| 2008/0021474 A1 * | 1/2008 | Bonutti | A61B 17/686 | 606/64 |
| 2008/0039845 A1 * | 2/2008 | Bonutti | A61B 17/0401 | 606/62 |
| 2008/0045962 A1 * | 2/2008 | Aeschlimann | A61B 17/00491 | 606/86 A |
| 2008/0065153 A1 * | 3/2008 | Allard | A61B 17/064 | 606/219 |
| 2008/0065154 A1 * | 3/2008 | Allard | A61B 17/064 | 606/219 |
| 2008/0109080 A1 * | 5/2008 | Aeschlimann | A61B 17/0401 | 623/16.11 |
| 2008/0161808 A1 * | 7/2008 | Fox | A61B 17/0642 | 606/75 |
| 2008/0172088 A1 * | 7/2008 | Smith | A61B 17/064 | 606/219 |
| 2008/0200955 A1 | 8/2008 | Tepic | | |
| 2008/0319443 A1 * | 12/2008 | Focht | A61B 17/0642 | 606/75 |
| 2009/0018560 A1 * | 1/2009 | Mayer | A61F 2/30721 | 606/151 |

(56) References Cited

U.S. PATENT DOCUMENTS

| | | | |
|---|---|---|---|
| 2009/0076617 A1* | 3/2009 | Ralph | A61B 17/688 623/17.19 |
| 2009/0131947 A1* | 5/2009 | Aeschlimann | A61B 17/0401 606/93 |
| 2009/0287249 A1* | 11/2009 | Reynolds | A61B 17/7059 606/246 |
| 2010/0023057 A1* | 1/2010 | Aeschlimann | A61B 17/0401 606/246 |
| 2010/0094358 A1* | 4/2010 | Moore | A61B 17/0642 606/319 |
| 2010/0241165 A1* | 9/2010 | Konieczynski | A61B 17/7071 606/248 |
| 2010/0241229 A1* | 9/2010 | Baehre | A61B 17/00491 623/16.11 |
| 2010/0274358 A1* | 10/2010 | Mueller | A61B 17/7059 623/17.16 |
| 2010/0292719 A1* | 11/2010 | Ducharme | A61B 17/064 606/151 |
| 2011/0118744 A1* | 5/2011 | Lehmann | A61B 17/0401 606/104 |
| 2011/0160766 A1* | 6/2011 | Hendren | A61B 17/0487 606/232 |
| 2012/0022535 A1* | 1/2012 | Mayer | A61B 17/1682 606/75 |
| 2012/0059429 A1* | 3/2012 | Voisard | A61B 17/0401 606/313 |
| 2012/0129131 A1* | 5/2012 | Baehre | A61B 17/00491 433/173 |
| 2012/0289964 A1* | 11/2012 | Nakaji | A61B 17/1695 606/80 |
| 2013/0190827 A1 | 7/2013 | Butters | |
| 2013/0226252 A1* | 8/2013 | Mayer | A61B 17/0642 606/331 |
| 2013/0304123 A1* | 11/2013 | Mayer | A61B 17/0642 606/246 |
| 2014/0214037 A1* | 7/2014 | Mayer | A61B 17/0642 606/75 |
| 2014/0277568 A1* | 9/2014 | Baehre | A61B 17/00491 623/23.47 |
| 2014/0309639 A1* | 10/2014 | Averous | A61B 17/0642 606/75 |
| 2015/0119993 A1* | 4/2015 | Mayer | A61B 17/1682 623/18.11 |
| 2015/0196291 A1* | 7/2015 | Voisard | A61B 17/0401 606/304 |
| 2016/0058579 A1* | 3/2016 | Aeschlimann | A61B 17/0401 623/17.16 |
| 2016/0106483 A1* | 4/2016 | Mayer | A61B 17/0642 606/297 |
| 2016/0135961 A1* | 5/2016 | Aeschlimann | A61B 17/0401 623/17.12 |

FOREIGN PATENT DOCUMENTS

| | | | |
|---|---|---|---|
| WO | 2010/045749 | 4/2010 | |
| WO | WO-2010045749 A1 * | 4/2010 | A61B 17/1617 |
| WO | 2010/096942 | 9/2010 | |
| WO | 2012/040863 | 4/2012 | |
| WO | 2013/006833 | 1/2013 | |

* cited by examiner

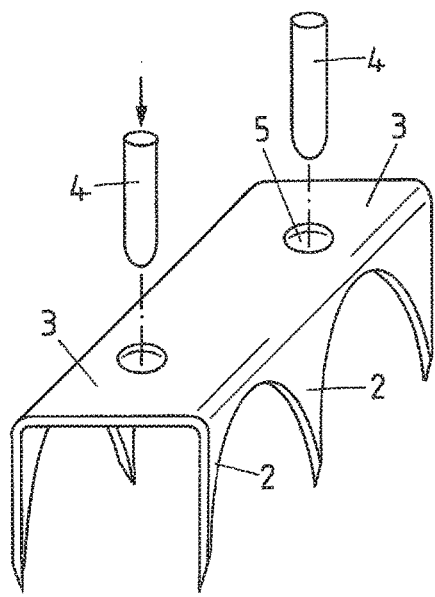
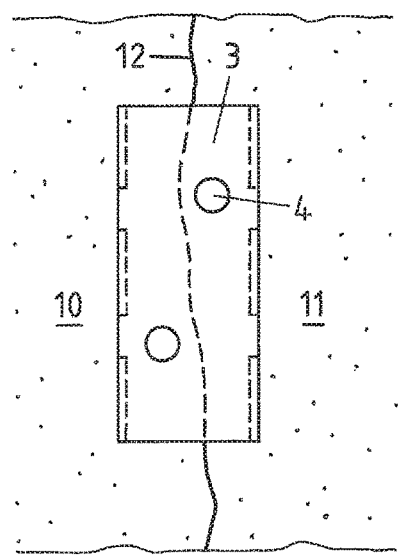
Fig. 3A
Fig. 3B
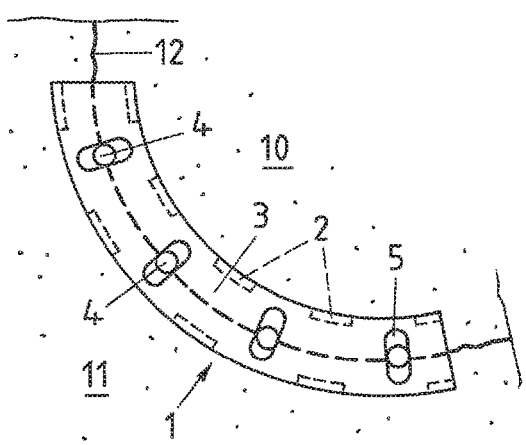
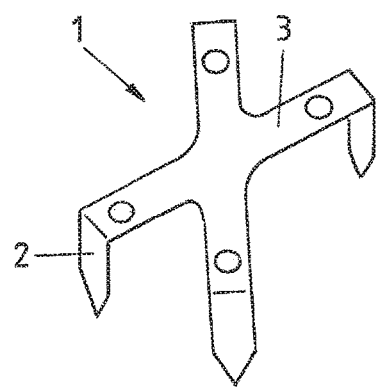
Fig. 3C
Fig. 4

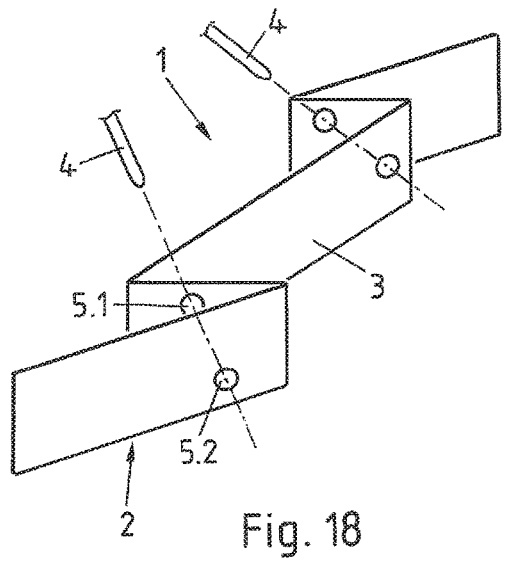
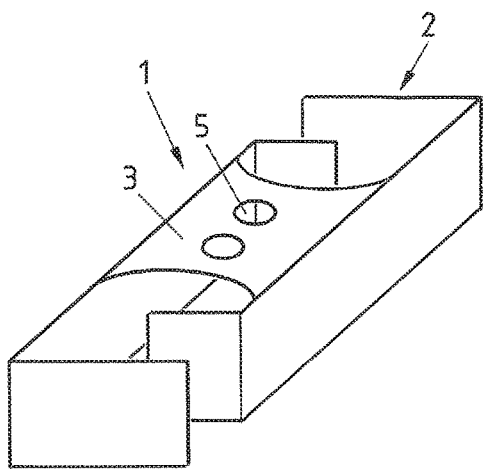
Fig. 18  Fig. 19
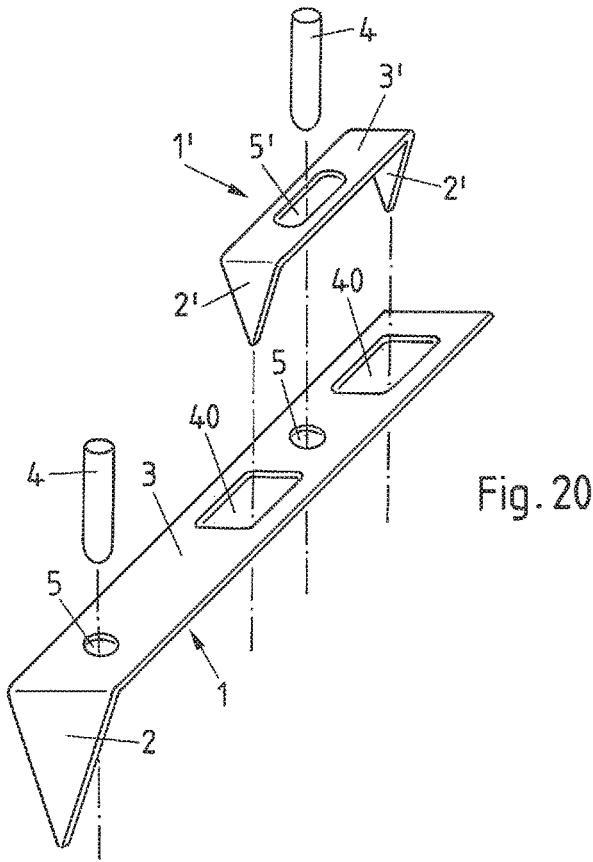
Fig. 20

METHOD AND IMPLANT FOR STABILIZING SEPARATED BONE PORTIONS RELATIVE TO EACH OTHER

BACKGROUND OF THE INVENTION

Field of the Invention

The invention is in the field of medical technology and concerns a method and an implant for stabilizing a plurality of separated bone portions relative to each other in a human or animal patient, wherein the bone portions to be stabilized are in particular two bone portions being separated by osteotomy or fracture but may also be two originally articulating bones to be immobilized relative to each other (joint fusion, in particular fusion of small joints such as e.g. facet joints, finger or toe joints).

Description of Related Art

Osteotomy is a surgical procedure in which a bone is cut with the aim of being shortened, lengthened or re-aligned. Osteotomy is performed on human and animal patients mainly for realigning the load bearing surfaces in joints and for realigning bone portions in particular in the faciomaxillar region but also for re-aligning bone portions healed together with an undesired alignment relative to each other after a fracture. The bone portions separated by the osteotomy procedure mostly need to be aligned in a desired position relative to each other and to be stabilized in this position for being able to heal together again. According to the state of the art, osteotomy sites are usually stabilized with the aid of a plate (e.g. metal plate) which is positioned on the bone surface across the osteotomy cut and is fastened on each side thereof with the aid of bone screws which extend through the plate into the bone tissue. According to the state of the art simple bone fractures are stabilized and small joints are immobilized in the same manner.

Well known applications of osteotomy concern e.g. human hip or knee joints and serve for re-aligning the articular surfaces of the joint in order to correct dysplasias and deformities by improvement of the alignment and/or the interaction of the articulating bones, or for relieving arthritic pain by re-aligning partly damaged articular surfaces to shift the bearing of the load from damaged to still healthy regions of the articular surfaces. Further well known osteotomy applications concern mandible or maxilla re-alignment e.g. for correcting discrepancies in tooth positions, or concern the chin bone for correcting or improving a person's profile. In veterinary medicine osteotomy is used e.g. for treating canine stifle joints suffering from cranial cruciate ligament rupture or damage by tibial plateau leveling or tibial tuberosity advancement, both these treatments serving for reducing tibiofemoral shear forces during weight bearing, which shear forces become large enough for damaging the joint, when the cranial cruciate ligament is damaged.

Screw and plate systems are well established for stabilizing bone portions separated by a cut or fracture and for immobilizing joints, although they constitute severe constraints which in many cases prevent optimal solutions. The most important ones of these constraints are the necessarily circular cross section of the screws, the reduction of the ratio of the load bearing capability of the screws vs. their cross section due to the screw thread, and the fact that the plate is necessarily positioned on the bone surface and, for accommodation of the screw heads and for being able to keep plate and screw rigidly at a predetermined angle relative to each other, has in most cases a thickness which is larger than would be necessary for guaranteeing a satisfactory plate stiffness.

BRIEF SUMMARY OF THE INVENTION

It is the object of the invention to provide a further method and an implant for stabilizing, in a human or animal patient, a plurality of separated bone portions relative to each other, wherein the bone portions may be separated by a cut or fracture or may form a joint which is to be immobilized or fused, and wherein method and implant according to the invention, compared with the state of the art screw and plate systems, shall allow more flexibility regarding design and load distribution between implant portions, and, furthermore, shall allow implant embodiments which can be implanted flush with the bone surface.

The named objects are achieved by the method and the implant as defined in the independent claims.

The implant according to the invention comprises, in a similar manner as the screw and plate system according to the state of the art, at least two first implant portions (peg portions), which in the implanted state extend into the bone tissue of both bone portions to be stabilized, and a second implant portion (bridge portion) connecting the first implant portions to form, at least in the implanted state, a substantially rigid assembly, wherein, in the implanted state, the bridge portion constitutes a bridge across the gap separating the two bone portions, i.e. bridges the cut, fracture or joint gap. While according to the state of the art the screws constituting the first implant portions principally serve for securing the implant in its implanted position and due to their design constraints have an only limited capability of counteracting forces acting on the implanted implant or the bone portions respectively, according to the invention, the first implant portions are non-threaded pegs which are virtually not capable of securing the implant in its implanted position (only little pull-out retention) but instead can be designed for a specific load bearing function, in particular for counteracting shear forces substantially parallel to a plane separating the two bone portions and forces or torque forcing the two bone portions away from each other or out of the desired alignment relative to each other.

For securing the assembly of peg and bridge portions of the implant according to the invention in its implanted position, i.e. for giving it the necessary pull-out retention, the implant further comprises at least one securing element which in cooperation with at least one securing structure comprised by the peg and bridge assembly prevents the implant from post-operative movement in a direction opposite the implantation direction. The securing element comprises a material having thermoplastic properties and constitutes a form-fit connection between the bone tissue and the securing structure(s) of the peg and bridge assembly through in situ liquefaction of the material having thermoplastic properties, through penetration of the bone tissue by the liquefied material and through re-solidification of the material having thermoplastic properties in the bone tissue.

The inventive separation of the force-counteracting function and the securing function between the peg and bridge assembly and the securing element(s) brings a number of advantages in comparison with the known screw and plate systems. These advantages mostly stem from the fact that the peg portions do not need a circular cross section nor a screw thread and they do not need to be rotated relative to the bridge portion on implantation, and from the fact that the design freedom regarding the peg portions allows more optimal load distribution in the implant and in the bone portions.

In the implant according to the invention the peg portions may have cross sections adapted to specific load bearing functions (e.g. T, U or double T cross section). Furthermore, for bearing similar loads, the cross section of the peg portions can be smaller than the cross section of corresponding screws and therefore necessitate less bone tissue removal for implantation and allow implantation at smaller distances from each other. Furthermore, it is possible to manufacture peg portions and bridge portions of the implant according to the invention from easily available sheet material, the peg and bridge portion assembly possibly being manufactured from one single piece of such sheet material. Such manufacturing is very simple and efficient regarding material and can therefore be carried out at relevantly reduced costs compared with the state of the art plate and screw systems.

For implanting the implant according to the invention, the bone portions are preliminarily stabilized relative to each other in a manner as well known from stabilization procedures using the state of the art screw and plate systems. Then, openings in the bone tissue for the peg portions and possibly also for the securing element(s) and the bridge portion are provided and the peg and bridge assembly is positioned relative to the bone portions. For securing the peg and bridge assembly in this position, the at least one securing element is positioned relative to the securing structure(s) of the peg and bridge assembly, energy (preferably mechanical vibration energy) is coupled into the securing element and therewith the material having thermoplastic properties is liquefied in situ and made to penetrate into the bone tissue. As soon as the material having thermoplastic properties is re-solidified the means for preliminary stabilization are removed and the operation site is closed.

The openings provided in the bone tissue for accommodation of the peg portions do not need to be dimensioned for press-fitting the peg portion in the opening. Depending on the form of the peg portions and on the mechanical properties of the bone tissue in which the peg portions are to be positioned it is possible also to not provide openings for the peg portions or to provide such openings in the cortical bone layer only, and to impact the peg portions into the bone tissue or into the cancellous bone tissue respectively. It is possible also to provide such openings (pilot bores) having a cross section which is substantially smaller and/or of a different shape than the over all cross section of the peg portions and to impact the peg portions into the openings.

If the peg portions are to extend parallel to each other, the assembly of peg and bridge portions is pre-assembled or even made as one piece. If the peg portions are to extend non-parallel to each other or if the surgeon is to be enabled to adapt the angle between the peg portions to a specific operation site, bridge portion and peg portions may be positioned relative to the bone portions in succession and may be assembled in situ, wherein means for locking each peg portion relative to the bridge portion for giving the peg and bridge assembly the necessary rigidity are provided.

The at least one securing element is positioned relative to the peg and bridge assembly when the assembly is positioned relative to the bone portions. In the preferred embodiments of the implant according to the invention the securing element is pin-shaped or staple-shaped and is e.g. fully made of the material having thermoplastic properties. The securing structures of the peg and bridge assembly to cooperate with the securing elements are e.g. through openings in assembly portions to extend on the bone surface, or notches in proximal edges of assembly portions extending substantially perpendicular to the bone surface.

The anchoring technique applied for anchoring the securing element in the bone tissue with the aid of a material having thermoplastic properties and energy, in particular vibrational energy, transmitted into the securing element for in situ liquefaction of the material having thermoplastic properties is disclosed e.g. in the publications U.S. Pat. Nos. 7,008,226, 7,008,226, US-2006/0105295, US-2008/109080, and US-2009/131947. The disclosure of all the named publications in its entirety is enclosed herein by reference. Therein the thermoplastic material needs to have mechanical properties suitable for a mechanically satisfactory anchorage of the securing element in the bone tissue, and, in its liquefied state, a viscosity which enables it to penetrate into natural or beforehand provided pores, cavities or other structures of the bone tissue. Advantageously, an only relatively small amount of the material is liquefied such that no unacceptable thermal load is put on the tissue.

Suitable liquefaction connected with an acceptable thermal loading of the tissue and giving suitable mechanical properties to the positive fit connections is achievable by using materials with thermoplastic properties having an initial modulus of elasticity of at least 0.5 GPa and a melting temperature of up to about 350° C. and by providing such material e.g., on a surface of the securing element, which on implantation is pressed against the bone tissue (as disclosed in U.S. Pat. No. 7,335,205 or 7,008,226) e.g. by forcing the securing element into a bone opening which is slightly smaller than the securing element or by expanding the securing element in a bone opening which originally is slightly larger than the securing element (expansion e.g. by mechanically compressing or buckling the securing element), or against another counter element (as disclosed in US 2009/131947).

During implantation, the securing element is subjected to vibration of a frequency preferably in the range of between 2 and 200 kHz (preferably ultrasonic vibration) by applying e.g. the sonotrode of an ultrasonic device to it. Due to the relatively high modulus of elasticity the thermoplastic material transmits the ultrasonic vibration with such little damping that inner liquefaction and thus destabilization of the securing element does not occur, i.e. liquefaction occurs only where the liquefiable material is in contact with the bone tissue or another counter element and is therewith easily controllable and can be kept to a minimum.

It is possible also to exploit energy types other than vibrational energy for creating the local thermal energy needed for the in situ liquefaction of the material having thermoplastic properties. Such other energy types are in particular rotational energy turned into friction heat in substantially the same manner as the vibrational energy, or electromagnetic radiation (in particular laser light in the visible or infrared frequency range), which radiation is preferably guided through the material with thermoplastic properties and locally absorbed by an absorber being contained in the material having thermoplastic properties or being arranged adjacent to this material (as e.g. disclosed in the publication US 2009/131947).

Materials having thermoplastic properties suitable for the at least one securing element of the implant according to the invention are e.g. thermoplastic polymers, e.g.: resorbable polymers such as polymers based on lactic and/or glycolic acid (PLA, PLLA, PGA, PLGA etc.) or polyhydroxy alkanoates (PHA), polycaprolactone (PCL), polysaccharides, polydioxanes (PD) polyanhydrides, polypeptides or corresponding copolymers or composite materials containing the named polymers as a component; or non-resorbable polymers such as polyolefines (e.g. polyethylene), polyacrylates, polymetacrylates, polycarbonates, polyamides, polyester, polyurethanes, polysulfones, polyarylketones, polyimides, polyphenylsulfides or liquid crystal polymers LCPs, polyacetales, halogenated polymers, in particular halogenated polyolefines, polyphenylensulfides, polysulfones, polyethers or equivalent copolymers or composite materials containing the named polymers as a component.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonateurethane (in particular Bionate by DSM, in particular type 65D and 75D). An overview table of polymers and applications is listed in Wintermantel, page 150; specific examples can be found in Wintermantel page 161 ff. (PE, Hostalen Gur 812, Höchst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff (POM—Polyacetal, tradenames Delrin, Tenac, has also been used in endoprostheses by Protec).

The material having thermoplastic properties may further contain foreign phases or compounds serving further functions. In particular, the thermoplastic material may be strengthened by admixed fibers or whiskers (e.g. of calcium phosphate ceramics or glasses) and such represent a composite material. The material having thermoplastic properties may further contain components which expand or dissolve (create pores) in situ (e.g. polyesters, polysaccharides, hydrogels, sodium phosphates), compounds which render the securing element opaque and therewith visible for X-ray, or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

Fillers used may include degradable, osseostimulative fillers to be used in degradable polymers, including: β-Tricalciumphosphate (TCP), Hydroxyapatite (HA, <90% crystallinity); or mixtures of TCP, HA, DHCP, Bioglasses (see Wintermantel). Preferred composite materials containing such fillers are: PLDLA (Böhringer: LR706) filled with dibasic calciumphosphate (weight ratio 70:30) and PLLA (Böhringer: L210S) filled with TCP (weight ratio: 40:60).

Osseo-integration stimulating fillers that are only partially or hardly degradable, for non degradable polymers include: Bioglasses, Hydroxyapatite (>90% cristallinity), HAPEX®, see S M Rea et al., J Mater Sci Mater Med. 2004 September; 15(9):997-1005; for hydroxyapatite see also L. Fang et al., Biomaterials 2006 July; 27 (20):3701-7, M. Huang et al., J Mater Sci Mater Med 2003 July; 14 (7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21 (4):351-74), J A Juhasz et al. Biomaterials, 2004 March; 25 (6):949-55. Particulate filler types include: coarse type: 5-20 μm (contents, preferentially 10-25% by volume), sub-micron (nanofillers as from precipitation, preferentially plate like aspect ratio>10, 10-50 nm, contents 0.5 to 5% by volume).

The peg and bridge assembly of the implant according to the invention are preferably made of a metal such as e.g. titanium or a titanium alloy or of a ceramic material such as e.g. aluminum oxide or zirconium oxide, but may also be made of a bio-degradable or non bio-degradable polymer material possibly containing a filler in form of fibers or particles for enhancing mechanical stability. If the peg and bridge assembly of the implant according to the invention are made of a non-degradable material and are designed for remaining in the patient's body, surfaces to be in contact with bone tissue are preferably equipped for enhancing osseointegration in a per se known manner by comprising a suitable roughness or structure and/or a suitable coating. Furthermore, such assemblies may comprise retention structures such as e.g. through openings or suitable surface structures which after a corresponding bone growth are suitable to form a positive fit connection in cooperation with the new bone tissue. If the implant is to be removed after healing of the cut or fracture or after fusion of the joint by osseoconduction, surfaces of the peg and bridge assembly are advantageously equipped for discouraging osseointegration (e.g. being polished) and the securing elements are made of a biodegradable material.

BRIEF DESCRIPTION OF THE DRAWINGS

The invention is described in further detail in connection with the appended Figs., wherein:

FIG. 3A is a perspective view that further illustrates an exemplary embodiment of the implant according to the invention;

FIGS. 3B-3C are sectional views that further illustrate an exemplary embodiment of the implant according to the invention;

FIG. 4 is a perspective view that further illustrates an exemplary embodiment of the implant according to the invention;

FIGS. 18 and 19 are perspective views that show further exemplary embodiments of peg and bridge assemblies in which features of assemblies according to previous Figs. are combined;

FIG. 20 is a perspective view that shows a further exemplary embodiment of the implant according to the invention in which one of the peg portions is constituted by an additional peg and bridge assembly;

In all figures same elements are denominated with same reference numerals.

DETAILED DESCRIPTION OF THE INVENTION

Figure 1A:
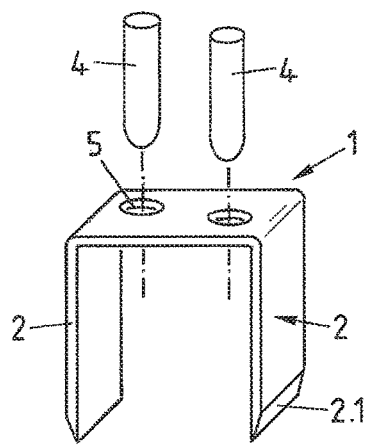
FIG. 1A is a perspective view that illustrates an exemplary embodiment of the implant.
Figure 1B:
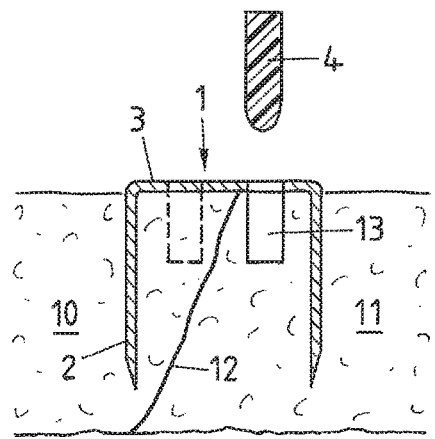
FIGS. 1B-1C are sectional views that illustrate an exemplary embodiment of the implant according to the invention, the implant comprising a peg and bridge assembly and a securing element, wherein the bride portion is to be positioned on the bone surface of the bone portions to be stabilized.
Figure 1C:
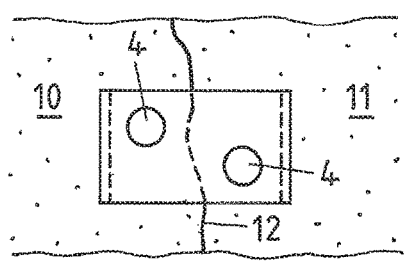

FIGS. 1A, 1B and 1C (FIGS. 1A/B/C) illustrate a first exemplary embodiment of the method and implant according to the invention, FIG. 1A showing the implant before implantation in a three dimensional illustration, FIG. 1B showing start (above) and end (below) of the implantation process in section parallel to the implantation direction, and FIG. 1C showing two separated bone portions being stabilized by the implant (viewed from above the bone surface).

The implant comprises a peg and bridge assembly 1 with two peg portions 2 and one bridge portion 3, and it further comprises two securing elements 4 (or only one securing element 4). The peg and bridge assembly 1 is preferably made of a single piece of sheet material, preferably sheet metal, the peg portions 2 being bent out of the plane of the bridge portion 3 parallel to each other and preferably comprising sharpened distal edges 2.1 tapering in the direction of the thickness of the sheet material and/or tapering in the direction of the width of the peg portion (not shown). The securing elements 4 are substantially pin-shaped and e.g. fully made of the material having thermoplastic properties, the pin cross section being adapted to the cross section of preferably a plurality of through openings 5 (securing structure) in the bridge portion 3.

The method for stabilizing two bone portions with the aid of the implant as shown in FIG. 1A is illustrated in FIG. 1B. The two bone portions 10 and 11, which are separated by a cut or fraction 12 or are cooperating in a joint to be immobilized or fused, are preliminarily fixated (means for preliminary fixation not shown) in the desired position relative to each other. The peg portions 2 are then impacted into the bone tissue of the two bone portions 10 and 11 such that the bridge portion 3 bridges the gap 12 separating the bone portions and substantially lies against the bone surface. If applicable, at least one blind bore 13 is then produced for introduction of the securing element(s) 4, wherein the bridge portion 3 or the through opening 5 respectively serves as template. The securing element 4, preferably attached to the distal end of a corresponding tool (not shown) is then introduced through the through opening 5 into the blind bore 13 and energy is supplied via the tool to the securing element 4 for the desired in situ liquefaction of the material having thermoplastic properties and for its penetration into the bone tissue of the wall of the blind bore or into undercut cavities or surface structures provided therein. During the same liquefaction process or in a further liquefaction or deformation process possibly using a different tool the proximal end of the securing element 4 may be shaped into a head resting on and possibly also being anchored in the outer surface of the bridge portion 3. Therein it is the choice of the surgeon to provide blind bores 13 and securing elements 4 anchored therein for all the through openings 5 or for only one of them or for only selected ones of them.

If the securing elements are simple pins of the material having thermoplastic properties and the used energy is vibrational energy, the blind bore 13 provided in the bone tissue is to be dimensioned such that the securing elements 4 need to be forced into the bores and the vibration coupled into the securing elements 4 produces friction between the bone tissue and the securing element and therewith the heat necessary for the in situ liquefaction of the material having thermoplastic properties. If a plurality of securing elements 4 are used, they can be anchored one after the other using a single-tip tool or they can be anchored simultaneously using a multi-tip (e.g. a fork-shaped) tool, wherein each anchoring element 4 is attached to one tool tip.

Figure 2A:
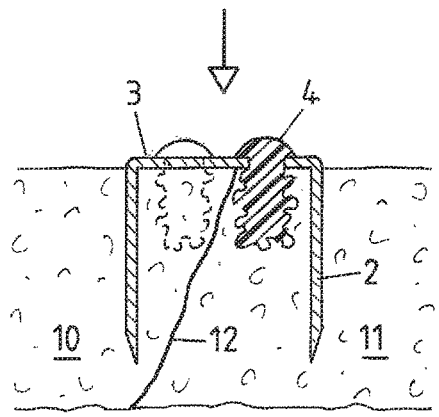
FIGS. 2A and 2B are sectional views that show a further exemplary embodiment of the implant according to the invention which is similar to the one shown in FIGS. 1A/B, but wherein the securing elements extend non-parallel to the peg portions.
Figure 2A:
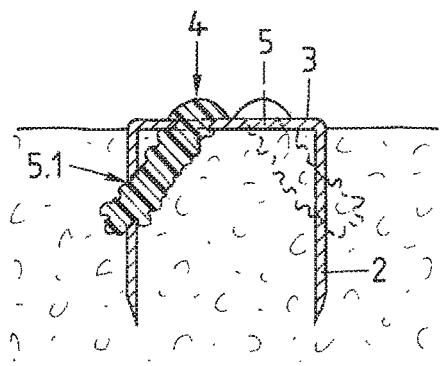
Figure 2B:
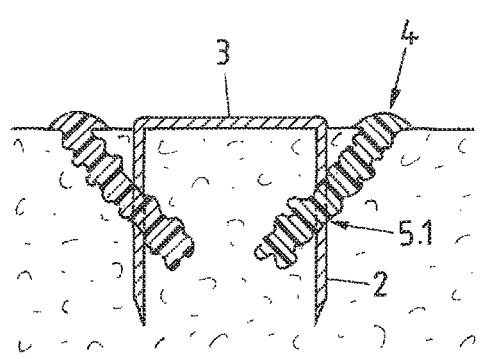

FIGS. 2A and 2B (FIGS. 2A/B) show in the implanted state a similar embodiment of the implant according to the invention as FIGS. 1A/B/C, wherein other than according to FIGS. 1A/B/C the securing elements 4 are not positioned at a right angle to the bridge portion 3 but at an acute angle. According to FIG. 2A, the securing elements 4 reach through the bridge portion 3 (through openings 5) and through the peg portions 2 (through openings 5.1) such that in addition to securing the peg and bridge assembly against movement out of the bone tissue, also reinforce the stiffness of this assembly, i.e. help to prevent further bending of the peg portions 2 relative to the bridge portion 3. According to FIG. 2B the securing elements 4 only reach through openings 5.1 in the peg portions. Such arrangement may be suitable if the bridge portion is very narrow or oriented substantially perpendicular to the bone surface as discussed further below (see in particular FIG. 18 and corresponding parts of the present description).

FIGS. 3A to 3C (FIGS. 3A/B/C) show further exemplary embodiments of the implant according to the invention (FIG. 3A: three dimensional illustration of the implant before implantation; FIGS. 3B and 3C: implanted implants viewed from above the bone surface). These further embodiments is based on the same principle as the embodiment illustrated in FIGS. 1A/B/C but differ therefrom by comprising a row of a plurality of peg portions 2 on either side of the bridge portion 3, which bridge portion extends between the two rows of peg portions substantially straight (FIGS. 3A and 3B) or non straight but e.g. adapted to a non-straight course of on osteotomy cut. FIG. 3C shows an example of such a bridge portion which extends along a circular curve and is therewith e.g. adapted for stabilizing canine tibial bone portions separated by osteotomy for tibial plateau leveling.

FIG. 3C also shows that the through openings 5 (securing structures) provided in the peg and bridge assembly 1 for accommodation of the securing elements 4 are not necessarily to be adapted to the cross section of the latter. As illustrated, the through openings 5 may be oblong and the securing elements 4 may have e.g. a circular cross section such that their position in the opening 5 can be selected by the surgeon to be e.g. either in one of the bone portions 10 or 11 or in the region of the line 12 separating the two bone portions, i.e. to be anchored in both bone sections. For final fixation of the securing elements 4 in the oblong through openings 5, the bridge portion may comprise structures to be penetrated by liquefied material of the securing element during the anchoring process or in a subsequent step. Such structure may e.g. be provided in the wall of the through openings 5 (e.g. groves extending substantially parallel to the surface of the bridge portion or cavities).

Implantation of the implants according to FIGS. 3A/B/C is substantially the same as discussed in connection with FIGS. 1A/B/C. Oblique orientation of the securing elements as shown in FIG. 2A/B is possible also.

FIG. 4 illustrates a further embodiment of the implant according to the invention of which only the peg and bridge assembly 1 is shown. The bridge portion 3 of this embodiment is cross-shaped comprising at the end of all four extensions one peg portion 2. The embodiment according to FIG. 4 is suitable not only for stabilizing two bone portions but also for stabilizing, e.g. three or four bone portions.

The embodiments of the invention as shown in FIGS. 1A/B/C, 2A/B, 3A/B/C, and 4 can be varied in the following manner without departing from the basic idea of the invention.

The angle between peg portions 2 and bridge portion 3 may differ from a right angle.

The peg and bridge assembly 1 may be made from an U-profile (e.g. extruded) by cutting and possibly forming the peg portions instead of from a sheet material by punching and bending.

The peg and bridge assembly 1 may be made from a sheet material, the peg and/or bridge portions being further stiffened by suitable forming of the sheet material (for examples see FIGS. 23 to 30).

The through opening(s) 5 in the bridge portion 3 (or in the peg portions, see FIG. 2B) and possibly corresponding blind bore(s) 13 may have a non-circular cross section, the securing element(s) 4 possibly also having a non-circular cross section.

There may be different numbers of peg portions 2 on either side of the bridge portion 3.

The peg and bridge assembly 1 may be asymmetric regarding also the form of the peg portions on either side of the bridge portion, wherein selected ones of the peg portions on one or the other side of the bridge portion may be equipped for being retained in the bone tissue not by simple impaction but e.g. by a screw thread or with the aid of in situ liquefaction of a material having thermoplastic properties.

Implants similar to the one shown in FIGS. 3A and 3B may be positioned with the elongate bridge portion 3 extending substantially perpendicular to the gap 12, the gap extending between peg portions 2 or across peg portions.

The peg and bridge assembly 1 is not made of one piece but the peg portions and the bridge portion are e.g. welded or soldered together, wherein the peg portions 2 may have other than elongated cross sections and/or the bridge portion 3 may protrude laterally beyond the peg portions 2.

The peg and bridge assembly 1 may comprise separate peg and bridge portions designed for being assembled in situ, the peg portions 2 e.g. being positioned through corresponding through openings in the bridge portion 3 and being locked therein e.g. by ultrasonic welding, wherein the through openings 5 in the bridge portion 3 and the proximal ends of the peg portions may be shaped to allow various angles between bridge portion and peg portion.

The elongated bridge portion 3 of the peg and bridge assembly 1 as shown in FIGS. 3A/B/C may comprise wider areas, on which the peg portions 2 and through openings 5 are arranged, and alternating therewith narrower portions being suitable for in-plane and possibly also out-of-plane plastic deformation by the surgeon for adapting the shape of the peg and bridge assembly to the course of the gap separating the two bone portions on the bone surface or to the form of the bone portions (as e.g. described in the publication US 2008/200955 to Tepic, Kyon).

The securing element 4 may comprise a head to start with and is introduced into the blind bore 13 deep enough for the head to abut against the outer surface of the bridge portion 3.

The securing element 4 may be connected to the bridge portion 3 not through a head but by the material having thermoplastic properties being forced in its liquid state into a suitable surface structure in the through opening 5 of the bridge portion 3, e.g. a suitable roughness or a thread.

The bridge portion 3 comprises pairs of through openings 5 and the two legs of a staple-shaped securing element are introduced through the two openings of each pair of openings (see also FIG. 20).

The securing element 4 may comprise a core of a material of a higher strength than the material having thermoplastic properties, wherein the core constitutes the distal end of the securing element, which is pointed and therewith suitable for being forced into bone tissue without the need of providing the blind bore 13 therein.

Figure 5A:
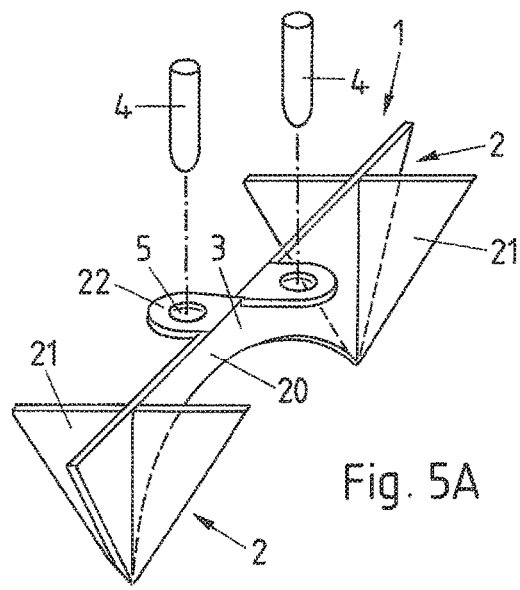
FIG. 5A is a perspective view and FIG. 5B is a plan view that illustrate an exemplary embodiment of the implant according to the invention, the implant comprising a peg and bridge assembly and securing elements, wherein the bridge portion is to extend within the bone tissue of the bone portions to be stabilized.
Figure 5B:
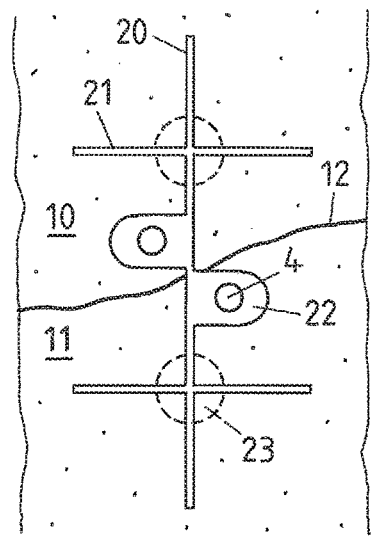

Before positioning the peg portions 2 in the bone tissue corresponding openings are provided in the bone tissue, wherein the cross section of the openings corresponds substantially with the cross section of the peg portions such that the peg portions can be introduced into the opening without substantial force or wherein the cross section of the openings (pilot bores) is smaller and possibly of a different shape than the cross section of the peg portions such that the peg portions need to be impacted into the openings (see e.g. FIG. 5B).

For forcing the two separated bone portions against each other, the bridge portion 3 may in a per se known manner comprise at least one slot extending substantially perpendicular to the gap separating the bone portions, wherein the bridge portion 3 and the slot are dimensioned for a tool (similar to a screw driver) to be inserted in the slot and, on rotating the tool in the slot, to widen the slot and therewith shorten the extension of the bridge portion 3 between the two peg portions 2 or the two rows of peg portions respectively. Therein the securing element 4 may be introduced into the bone tissue through the widened slot.

For allowing limited movement of the two bone portions relative to each other after implantation of the implant, the bridge portion may comprise two parts and means for moving the two parts relative to each other and for securing them in a desired position relative to each other. An exemplary application of such post-implantation movement is the pivoting apart of the portions of a vertebral body being at least partly separated by a compression fracture or osteotomy for treating kyphosis, wherein the implant according to the invention is implanted on a lateral side of the vertebral body, the two bridge parts then being pivoted against each other around a posterior pivot axis such opening the vertebral body on its anterior side. For pivoting the bridge parts and for locking the bridge parts in a desired pivoting position the pivot axis may e.g. be equipped as a ratchet.

FIGS. 5A and 5B (FIGS. 5A/B) show a further exemplary embodiment of the implant according to the invention, FIG. 5A being a three dimensional illustration of the implant before implantation and FIG. 5B showing the implant after the implantation process (viewed from above the bone surface). The implant according to FIGS. 5A/B again comprises a peg and bridge assembly 1 with two peg portions 2 and one bridge portion 3 and is preferably made of a sheet material (e.g. sheet metal), wherein a first piece 20 of the sheet material constitutes the bridge portion 2 and part of the peg portions 3 and wherein each peg portion comprises a second piece 21 of sheet material being oriented at an angle (e.g. right angle) to the first piece 20 of sheet material, such that the peg portions 2 have cross-shaped cross sections. Other than shown in FIGS. 1A/B/C, 2A/B, 3A/B/C, and 4, the bridge portion 2 of the implant according to FIGS. 5A/B is not oriented to lie on the bone surface but to extend from the bone surface into the bone tissue, its proximal edge being e.g. flush with the bone surface. Therein a depth to which the sheet pieces reach into the bone tissue is preferably, as illustrated, smaller for the bridge portion 3 than for the peg portions 2. The peg portions 2 may, as illustrated, be tapering towards their distal end and may comprise further sheet pieces forming together with the first and second sheet pieces an arrangement of a star-like cross section.

As securing structures, the first sheet piece 20 (and/or the second sheet pieces 21) comprises through openings 5 arranged in securing portions 22 protruding from the proximal edge of the sheet piece and being bent to extend parallel to the bone surface. The securing elements 4 are again preferably pin-shaped. The securing portions 22 which, besides their part in the securing function, may also serve for strengthening the bridge portion 2 against bending, may also consist of a further sheet piece (not shown) which is attached to the proximal edge of the first sheet piece 20 by e.g. welding or soldering (see also FIG. 7).

The method for implanting the implant as illustrated in FIGS. 5A/B is substantially the same as discussed in connection with FIGS. 1A/B/C, wherein depending on the density and mechanical strength of the bone tissue in which the implant is to be implanted and depending on the thickness of the sheet material and the form of the distal edge of the bridge portion 3 and the distal ends of the peg portions 2 it may or may not be desired or necessary to open at least a cortical bone layer on the bone surface for being able to impact the implant into the bone tissue. It may further be advantageous to provide pilot bores 23 for the peg portions 2 which pilot bores however need to have an only substantially smaller diameter and preferably depth than the peg portions 2 have.

Figure 6A:
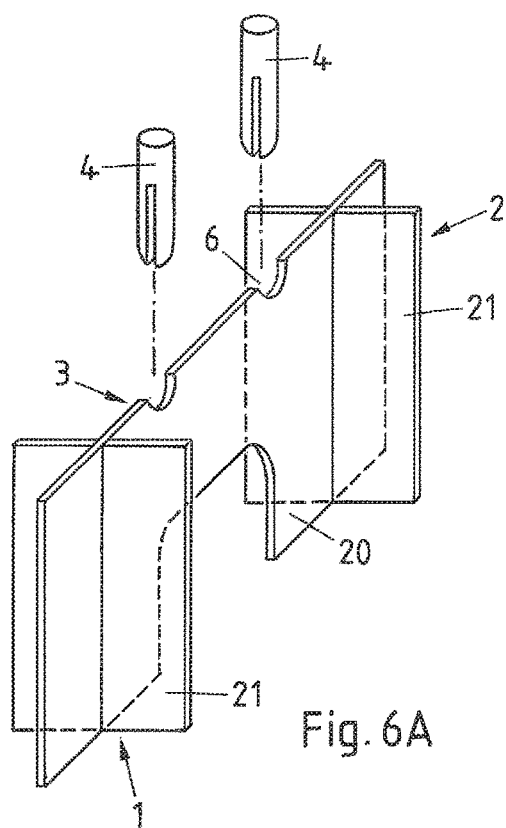
FIG. 6A is a perspective view and FIG. 6B is a sectional view that illustrate a further exemplary embodiment of the implant according to the invention based on the same principle as the embodiment as shown in FIGS. 5A/B.
Figure 6B:
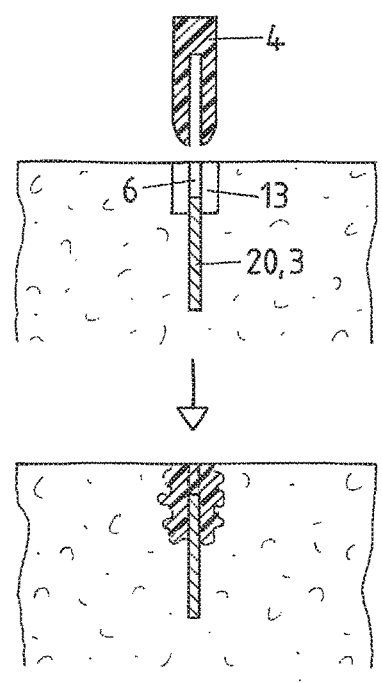

FIGS. 6A and 6B (FIGS. 6A/B) illustrate a further exemplary embodiment of method and implant according to the invention, wherein FIG. 6A is a three dimensional illustration of the implant before implantation and FIG. 6B illustrates in two sections parallel to the implantation direction the implantation process (above: before the implantation process, and below: after the implantation process). The implant according to FIGS. 6A/B differs from the implant according to FIGS. 5A/B mainly regarding the securing structures comprised by the peg and bridge assembly 1 and the securing elements 4. The securing elements 4 have the form of an axially slotted pin or of a staple and they preferably cooperate with notches 6 (securing structures) in the proximal edge of the first sheet piece 20 (and/or the second sheet pieces 21, not shown).

The implant according to FIGS. 6A/B is preferably implanted with proximal edges of the sheet pieces to be substantially flush with the bone surface, which means that the depth of the notches 6 is approximately the same as the axial length of the non-slotted section of the securing element 4. It is possible also to not provide the notches 6 (securing structure constituted by the proximal edge of the peg and bridge assembly only) and to implant the peg and bridge assembly 1 buried underneath the bone surface such that the securing element 4 can be implanted flush with the bone surface or to implant the peg and bridge assembly 1 flush with the bone surface and to let a proximal portion of the securing element 4 protrude above the bone surface.

The peg and bridge assemblies shown in FIGS. 5A/B and 6A/B are, as described above, assembled before being positioned in the bone portions. However, it is possible also to assemble them in situ, i.e. sheet piece after sheet piece, for which purpose the sheet pieces are provided with cooperating slots where they are to be crossed (slot in one sheet piece extending from the distal edge, slot in the other sheet piece extending from the proximal edge). For the implantation e.g. sheet piece 20 is first impacted and then sheet pieces 21. Such successive impaction necessitates less impaction force than simultaneous impaction as described above.

Figure 7:
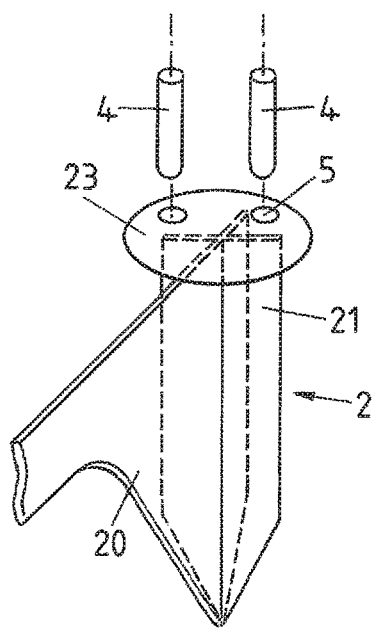
FIGS. 7 and 8 are perspective views that illustrate further exemplary embodiments of securing structures and securing elements cooperating therewith, the securing structures being applicable for implant embodiments as e.g. shown in FIGS. 5A/B and 6A/B.
Figure 8:
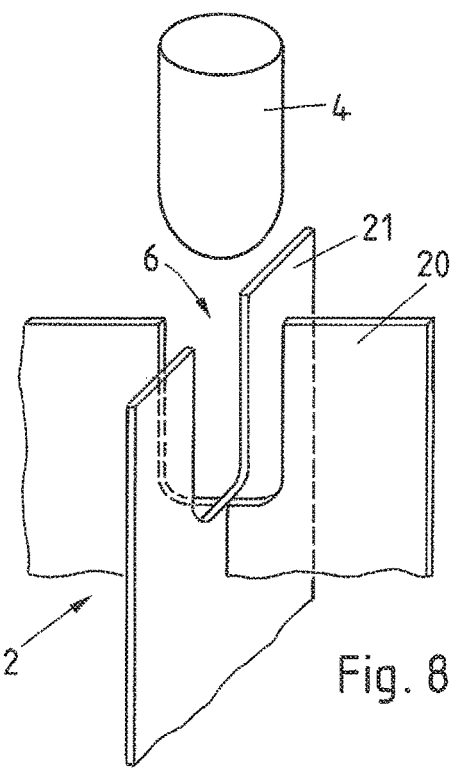

FIGS. 7 and 8 illustrate further embodiments of cooperating securing elements and securing structures arranged on peg portions of implants according to the invention, wherein not the entire implant but only one peg portion 2 and the cooperating securing element(s) 4 are shown.

The peg portion 2 of FIG. 7 is substantially the same as the peg portions as illustrated in FIGS. 5A/B and 6A/B, i.e. being constituted by a first sheet material piece 20 and a second sheet material piece 21 but it further comprises a proximal cover piece 23 with at least one through opening 5 provided for cooperation with a substantially pin-shaped securing element 4.

The peg portion 2 according to FIG. 8 is constituted again by part of a first sheet material piece 20 and a second sheet material piece 21 wherein first and second sheet material pieces comprise notches 6 there, where proximal edges of the sheet material pieces cross each other. The two interacting notches 6 and a blind bore or removal of the bone tissue in the region of the interacting notches 6 constitute guidance for the securing element 4 which may comprise two distal grooves (not shown) adapted to the first and second sheet material pieces. If, as illustrated in FIG. 8, the securing element 4 does not comprise the named grooves, on being introduced into the notches, the securing element 4 or at least some of the liquefied material having thermoplastic properties is preferably forced past the notches such that the named grooves are formed during the implantation process.

Figure 9:
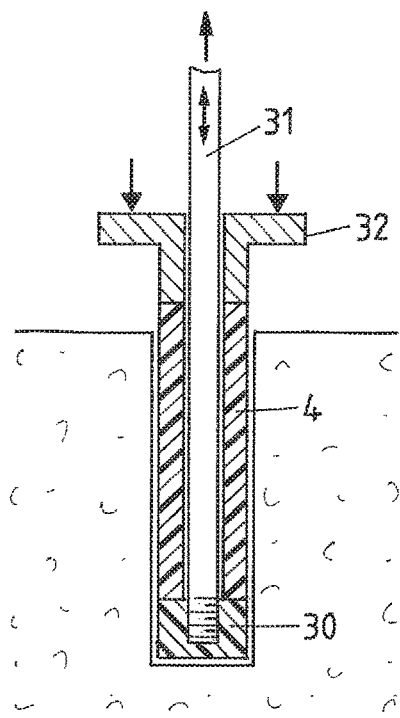
FIG. 9 is a sectional view that shows a further method for anchoring securing elements in the bone tissue of the bone portions to be stabilized relative to each other.
Figure 9:
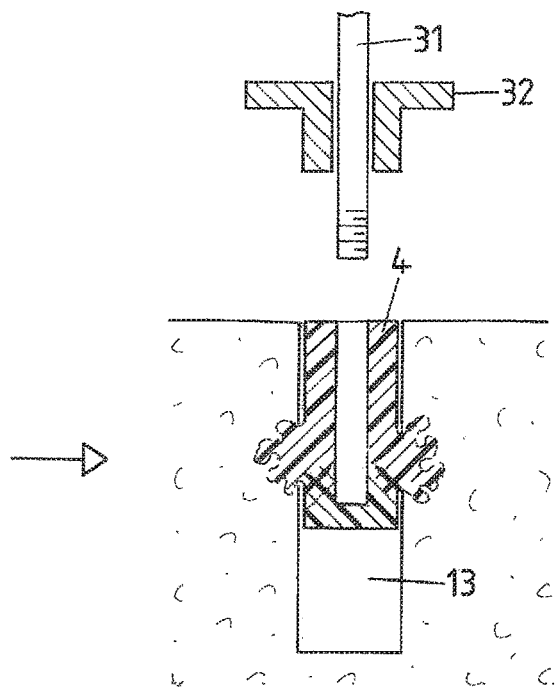

FIG. 9 illustrates a further method for in situ liquefaction of a securing element 4 applicable for securing a peg and bridge assembly relative to separated bone portions, wherein the method according to FIG. 9 is applicable e.g. in connection with the peg and bridge assemblies described above in which the securing structure is a through opening in an assembly portion. According to FIG. 9, the securing element 4 which comprises the material having thermoplastic properties is substantially tube-shaped and is held between a foot piece 30 of a vibrating tool 31 and a counter element 32, the vibrating tool extending through the lumen of the tube-shaped securing element 4 and being connected with the foot piece 30. By exerting forces directed against each other to tool 31 and counter element 32 while vibrating the tool 31 and therewith the foot piece 30, the securing element 4 is compressed and the material having thermoplastic properties of the securing element 4 is liquefied at the interface between the foot piece 30 and the securing element 4 and/or at the interface between the counter element 32 and the securing element 4 and is forced radially away from the named interfaces to penetrate into bone tissue situated adjoining the interface. Instead of vibrating the vibration tool 31 it is possible also to vibrate the counter element 32 and use the element designated in FIG. 9 as vibration tool as counter element. If the two named interfaces at which liquefaction is possible are of the same design, liquefaction will occur mainly at the interface between the securing element and the vibrating element. If liquefaction mainly at the other interface or only at the other interface is desired, this other interface is to be equipped with energy directors and/or the interface between the securing element and the vibrating element is to be eliminated by rigidly connecting the two elements.

According to FIG. 9 (left: before the liquefaction process, right: after the liquefaction process), the foot piece 30 comprises at least at its proximal face a material which is weldable or otherwise connectable to the securing element 4 during the liquefaction process and it is connected to the distal tool end by a connection which can be easily separated after the liquefaction process, such that on removal of the tool 31 after the liquefaction process, the foot piece 30 can be left in the bone tissue constituting part of the securing element. The foot piece 30 is preferably made of the same material as the securing element 4 such that it is welded to the securing element during the liquefaction process, and it is connected to the distal tool end by a form fit connection (e.g. cooperating threads) which can easily be destroyed when the material of the foot piece 30 gets warmed in the liquefaction process. The method as illustrated in FIG. 9 and briefly described above is described in detail in the publication US 2009/131947, the entire disclosure of which is enclosed herein by reference.

FIGS. 10 to 16 illustrate very schematically further exemplary embodiments of the implant according to the invention, wherein all these embodiments comprise a peg and bridge assembly 1 which is preferably made of a sheet material. In all FIGS. 10 to 16, the implant is shown in an implanted configuration (viewed from above the bone surface), in which the bridge portion 3 extends across the gap 12 separating the two bone portions 10 and 11. Small circles 30 show possible locations of cooperating securing elements and securing structures which are designed as e.g. shown in any of the embodiments described above, and which are not further described in connection with FIGS. 10 to 16.

Figure 10:
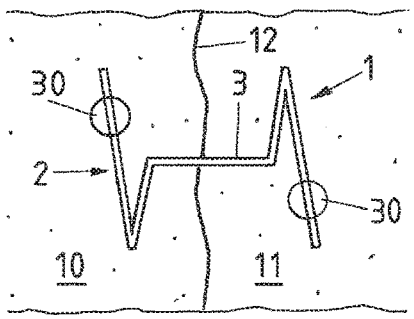
FIGS. 10-16 are plan views that show further exemplary embodiments of the implant according to the invention, which embodiments, the same as the embodiments according to e.g. 5A/B and 6A/B, are suitable for being manufactured from sheet material.
Figure 11:
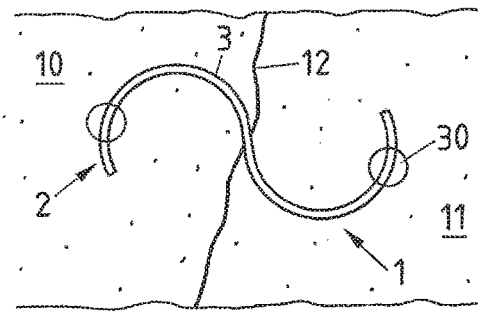
Figure 12:
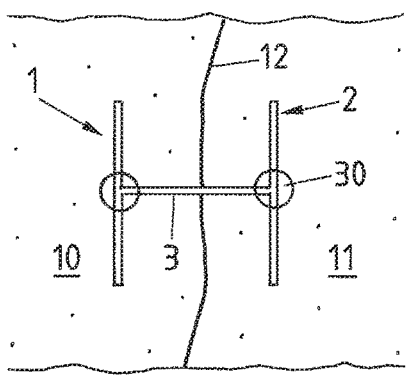
Figure 13:
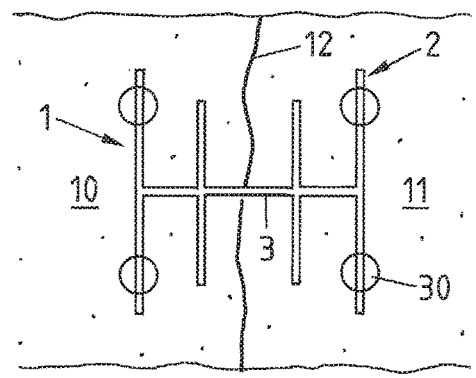
Figure 14:
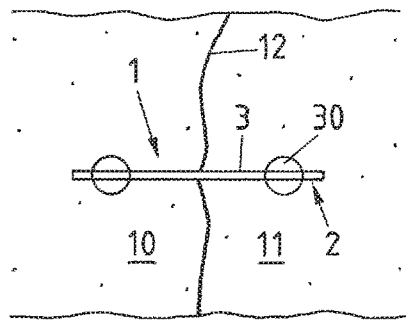
Figure 15:
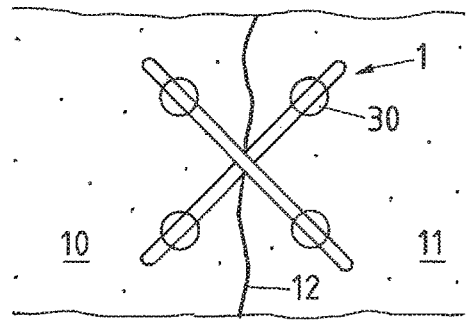

According to FIGS. 10 and 11, the peg and bridge assembly 1 consists of one only piece of sheet material, which is folded and/or bent in a plurality of places to form two peg portions 2 with a harmonica-like or just bent cross section and a bridge portion 3 connecting the two peg portions. The securing elements and securing structures (circles 30) are e.g. arranged on either end of the folded and/or bent piece of sheet material. According to FIG. 12, the peg portions 2 have a T-shaped cross section and the securing elements and structures (circles 30) are arranged at the center of the T-shape. According to FIG. 13, the peg portions 2 have a cross section in the shape of a double T, the securing elements and securing structures (circles 30) being e.g. arranged at the periphery thereof. According to FIG. 14, peg portions 2 and bridge portion 3 are all integrated in one single and substantially straight piece of sheet material, the securing elements and securing structures (circles 30) being arranged near the ends of this piece of sheet material. Other than the embodiments according to FIGS. 10 to 13, the embodiment according to FIG. 14 is in particular suitable for applications in which shear forces parallel to the paper plane of FIG. 14 between the two bone portions 10 and 11 are to be counteracted while other forces, in particular forces pulling the two bone portions away from each other, are of an only limited importance. The peg and bridge assembly according to FIG. 15 comprises two assemblies as shown in FIG. 14, wherein the sheet pieces cross each other and are assembled before implantation or are implanted in succession, i.e. assembled in situ as e.g. described in connection with FIGS. 5A/B and 6A/B. According to FIG. 16, the peg and bridge assembly 1 again comprises only one bent piece of sheet material constituting e.g. five peg portions 2 and three bridge portions 3, the securing elements and securing structures (circles 30) being arranged e.g. in the area of the peg portions.

Figure 16:
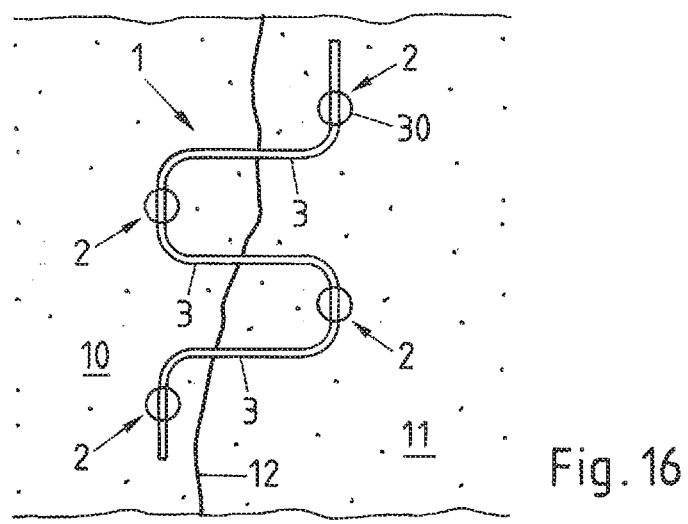
Figure 17:
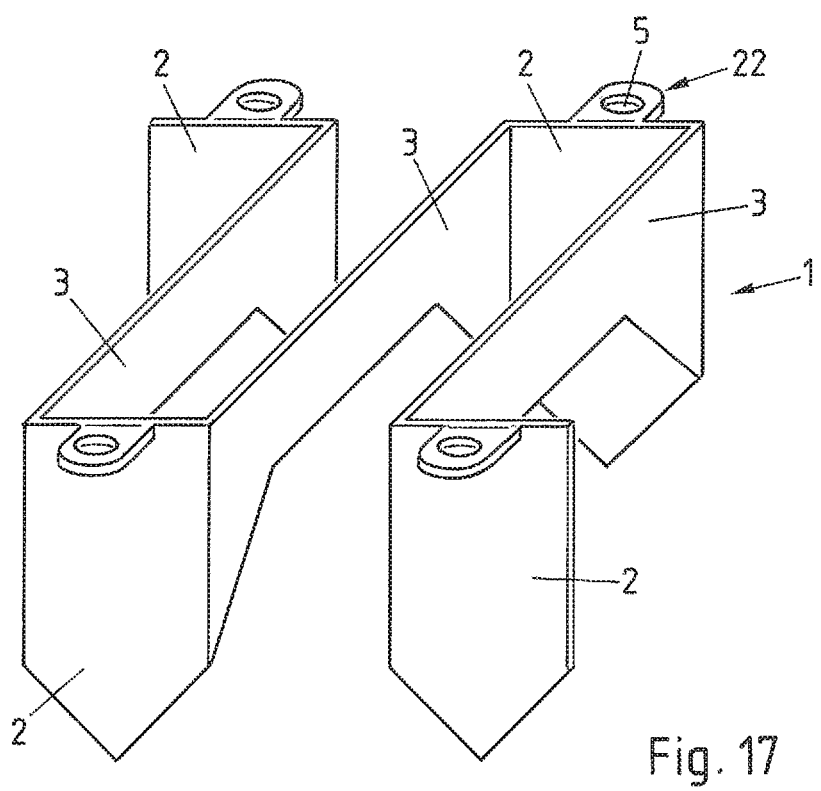
FIG. 17 is a perspective view that shows a further exemplary embodiment of the implant according to the invention.

FIG. 17 is a three dimensional illustration of the peg and bridge assembly 1 as schematically illustrated in FIG. 16 and being equipped with securing structures in the form of sheet material portions 22 protruding from the proximal edge of the assembly and being bent to extend parallel to the bone surface when the assembly is positioned relative to the bone portions. The protruding portions 22 comprise through openings 5 for accommodation of the securing elements.

FIGS. 18 and 19 illustrate examples in which features of above described embodiments can be combined in different ways.

The peg and bridge assembly 1 shown in FIG. 18 is substantially the same as the one shown in FIG. 10 but differs therefrom regarding the securing structures which in this case are not arranged on the proximal edge of the peg or bridge portions but are constituted by through openings 5.1 and 5.2 through assembly portions reaching into the bone tissue as already discussed in connection with FIGS. 2A/B. Pin-shaped securing elements are introduced through the openings 5.1 and 5.2 in a direction shown as dash-dotted lines. Blind bores to be provided for the securing elements 4 originate from the bone surface beside the peg and bridge assembly. Oblique securing elements as described in connection with FIGS. 2A/B and 18, which cooperate with through openings in assembly portions extending into the bone tissue (securing structures) are possible for all above described embodiments.

The peg and bridge assembly shown in FIG. 19 is in principle a combination of the assemblies as e.g. illustrated in FIG. 1A/B on the one hand and in FIG. 10 on the other hand. The peg and bridge assembly consists of one only sheet piece which is preferably made by punching and which is bent in two ways, firstly for forming a bridge portion 3 to extend on the bone surface and peg portions 2 to extend into the bone surface as shown in FIGS. 1A/B and secondly in planes angled to the plane of the bridge portion 3 for further forming of the peg portions as shown e.g. in FIG. 10.

FIG. 20 illustrates a further exemplary embodiment of method and implant according to the invention, for which the bridge portion 3 is to extend on the bone surface. The implant again comprises a peg and bridge assembly 1 (main assembly) which is shown in an exploded manner. The peg and bridge assembly 1 comprises one peg portion 2 rigidly attached to one side of the bridge portion 3 and instead of an additional peg portion rigidly attached to the one bridge portion 3 an additional peg and bridge assembly 1' (additional assembly) comprising an additional bridge portion 3' and rigidly attached thereto two additional peg portions 2'. Furthermore, the twin assembly (main and additional assembly) comprises e.g. two securing elements 4.

For the peg portions 2' of the additional assembly 1' being able to reach into the bone beneath the bridge portion 3 of the main assembly 1, the latter comprises one through opening (peg openings 40) for each one of the peg portions 2' of the additional assembly, wherein the peg openings 40 are advantageously dimensioned for allowing a plurality of different positions of the peg portions 2' therein. Furthermore, the bridge portion 3 of the main assembly 1 as well as the bridge portion 3' of the additional assembly 1' comprise through openings 5 and 5' for the securing element 4, wherein the through openings 5 and 5' are located such that they are aligned to each other, when the peg portions 2' of the additional assembly are located in the peg openings 40 and wherein preferably at least one of the through openings 5 and 5' is dimensioned such that the named alignment is possible for all possible peg positions 2' in the peg openings 40.

The implant according to FIG. 20 is implanted by impacting the peg portion 2 of the main assembly into the first one of the bone portions and retaining the main assembly relative to this first bone portion by anchoring the securing element 4 in the bone portion, by then, if applicable, positioning the second bone portion relative to the first one or adjusting the position of the second bone portion, by then impacting the peg portions 2' of the additional assembly 1' through the peg openings 40 of the main assembly into the second bone portion and by then retaining the additional assembly 1' and therewith also the main assembly 1 in the second bone portion and the two assemblies relative to each other by anchoring a securing element extending through the through openings 5 and 5' in the second bone portion. Therein, it is obviously possible for the peg portions 2' of the additional assembly 1' to finally extend into the bone tissue non-parallel to the peg portion 2 of the main assembly 1.

The implant according to FIG. 20 is in particular suitable for applications in which it may be advantageous if the relative position of the bone portions to be stabilized with the aid of the implant can be adjusted when the implant is already fixed to one of the bone portions, for which successive fixation of the implant in the two bone portions may be desired for other reasons, or for which non-parallel orientation of the peg portions is desirable. One such application is the surgery for tibial tuberosity advancement.

Variants of the embodiment according to FIG. 20 may e.g. comprise more than one peg portion 2 in the main assembly 1, more than one additional assembly 1', an additional assembly 1' with more than one peg portion 2', or all peg portion(s) 2 in the main assembly 1 replaced by additional assemblies 1'. Furthermore, features described in connection with FIGS. 1A/B/C, 2A/B, 3A/B/C and 4 are applicable also for the embodiment according to FIG. 20.

Figure 21:
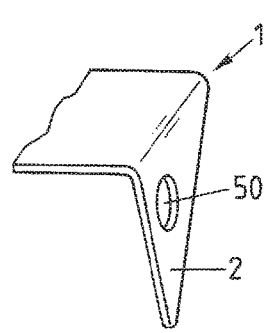
FIGS. 21 and 22 are perspective views that illustrate exemplary retention structures which are in particular suitable for embodiments of the implant according to the invention being manufactured from sheet material.
Figure 22:
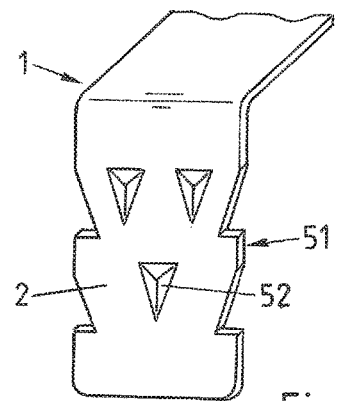

FIGS. 21 and 22 illustrate exemplary retention structures which are suitable in particular for embodiments of the peg and bridge assembly of an implant according to the invention, which peg and bridge assembly is made of sheet material substantially by punching and bending. These retention structures serve for retaining the implant in the bone tissue by constituting a positive-fit connection with new bone grown after the implantation, in particular at a time after the implantation when securing elements made of a biodegradable material are no more able to retain the implant in the bone tissue. The retention structures can be made in substantially the same manufacturing steps (punching and bending) as the peg and bridge assembly and therefore do not render manufacturing more costly as this is the case for retention structures of known implants serving the same purpose which usually have to be machined in an additional manufacturing step.

The retention structure according to FIG. 21 is a through retention opening 50 provided e.g. in a peg portion 2 of a peg and bridge assembly 1 similar to the one as illustrated in FIG. 1A/B/C. Bone growth after the implantation will reach through the opening 50 and retain the peg and bridge assembly in the bone material by a positive fit connection. Through retention openings 50 can be advantageously provided in any of the above described peg and bridge assemblies which are made of sheet material, not only on the peg portions but also on bridge portions reaching into the bone tissue.

FIG. 22 shows retention structures in the form of indented edges 51 and teeth 52 of e.g. a triangular shape made by deforming one edges of a slot provided in the sheet material to protrude from the sheet surface as well known from kitchen graters made of sheet material. It is possible also to produce retention structures by partly punching out forms, e.g. two sides of triangles, and fold such forms out of the main plane of the sheet material. On implantation the folded out forms are resiliently bent back into the plane of the sheet material and after implantation will be pressed back against or into the bone tissue. All the named retention structures can be fabricated in substantially the same manufacturing steps as the ones necessary for manufacturing the implant itself, i.e. without any additional effort. As in FIG. 21 the retention structure illustrated in FIG. 22 are shown to be located on a peg portion 2 of the peg and bridge assembly 1 but may also be provided on a bridge portion extending into the bone tissue.

FIGS. 23 to 30 illustrate exemplary structures for stiffening structures provided on a peg and bridge assembly of an implant according to the invention, the peg and bridge assembly being at least partly made of a sheet material. The structures are particularly suitable for bridge portions extending on the bone surface but, if applicable, may also be provided on peg portions and possibly on bridge portions extending into the bone tissue.

Figure 23:
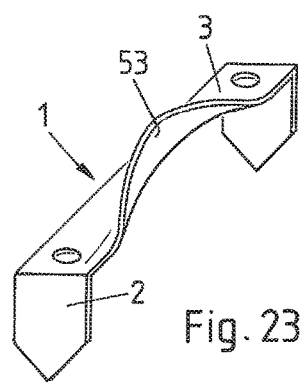
FIG. 23 is a perspective view that illustrates an exemplary stiffening structure that is suitable for embodiments of the implant according the invention being manufactured from sheet material and comprising a bridge portion to extend on the bone surface.
Figure 24:
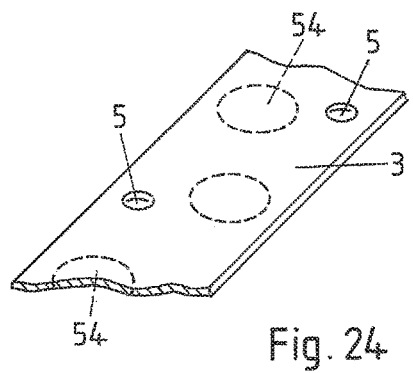
FIG. 24 is a perspective view that illustrates an exemplary stiffening structure.

FIG. 23 shows a peg and bridge assembly 1 similar to the one illustrated in FIGS. 1A/B/C whose bridge portion 3 comprises one edge 53 extending from one peg portion 2 to the other one which edge 53 is bent out of the main plane of the bridge portion for enhancing the stiffness of the bridge portion 3 to resist bending forces perpendicular to the main surfaces of the sheet material. FIG. 24 shows part of a sectioned bridge portion 3 comprising deformed locations in the form of bulges 54 which have a local stiffening effect and may, as illustrated, e.g. alternate with securing structures in the form of through openings 5.

Figure 27:
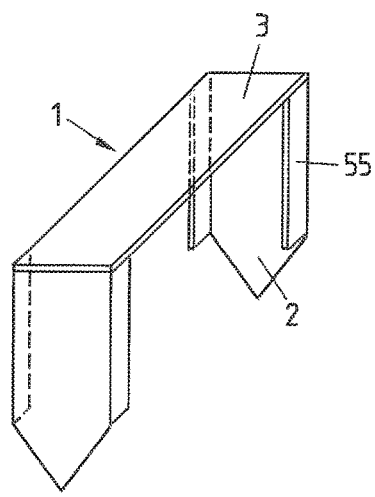
FIG. 27 is a perspective view that illustrates an exemplary stiffening structure.
Figure 25A:
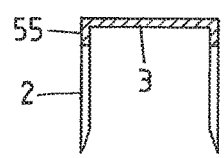
FIGS. 25A-26B are sectional views that illustrate an exemplary stiffening structure.
Figure 25B:
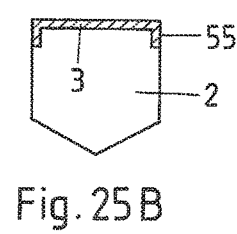
Figure 26A:
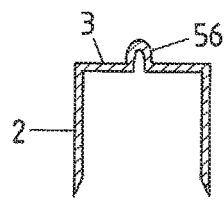
Figure 26B:
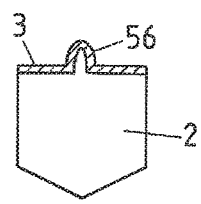

FIGS. 25A/B and 26A/B show in section further exemplary stiffening structures for stiffening a bridge portion 3 of a sheet material against bending forces substantially perpendicular to the main surfaces of the bridge portion 3. These stiffening structures are bent edge portions 55 (FIGS. 25A/B) or a folded ridge 56 (FIG. 26A/B) which bent edge portions 55 or ridge 56, depending on the dimensions of the bridge portion 3 and the application of the implant, may e.g. extend between opposite rows of peg portions 2 (FIGS. 25A and 26A) or extend in a direction from one peg portion to an opposite one (FIGS. 25B and 26B). FIG. 27 illustrates a peg and bridge assembly 1 made of a sheet material, whose peg portions 2 are stiffened by bent edges 55 extending parallel to an implantation direction. In the same way such peg portions 2 may be stiffened by a folded ridge as illustrated in FIGS. 26A/B.

Figure 28:
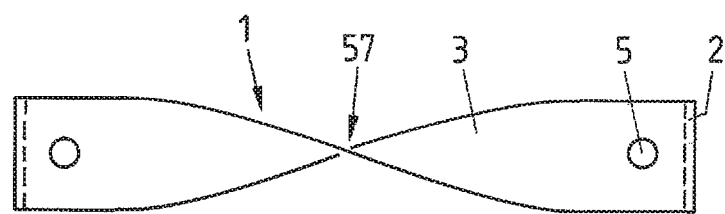
FIGS. 28-30 are plan views that illustrate an exemplary stiffening structure.
Figure 29:
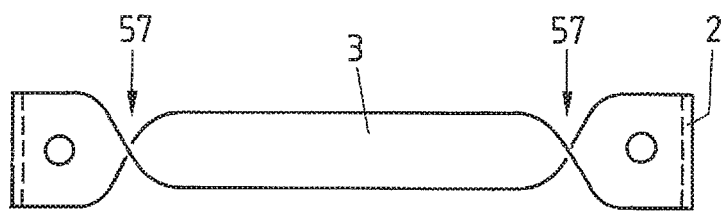
Figure 30:
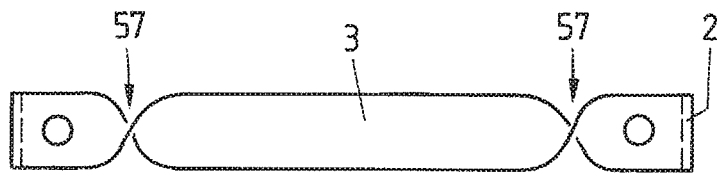

FIGS. 28 to 30 show further exemplary embodiments of stiffening structures which are suitable for bridge portions 3 of peg and bridge assemblies 1 of implants according to the invention, in particular for such bridge portions 3 made of a sheet material and having an elongated narrow form, wherein the stiffening is achieved by twisting the bridge portion 3. According to FIG. 28 the stiffening structure is a twist 57 of 180° which regards the whole middle part of the bridge portion 3. According to FIGS. 29 and 30 the bridge portion 3 comprises two lateral twists 57 which add up to 180° (FIG. 29) and leave a middle bridge part at an angle of less than 180° (e.g. 90°) relative to the lateral bridge parts, or add up to 360°, preferably twice 180° (FIG. 30) which leaves the middle bridge part in substantially the same plane as the lateral bridge parts. The stiffening structures according to FIGS. 28 to 30 are particularly suitable for peg and bridge assemblies as illustrated in FIGS. 1A/B/C, 2A/B and possibly 3A/B/C. the stiffening structures according to FIGS. 29 and 30 are particularly suitable for peg and bridge assemblies as illustrated in FIG. 4.

What is claimed is:

1. A method for stabilizing, in a human or animal patient, at least two bone portions relative to each other, the method comprising the steps of:
    providing an implant, said implant comprising at least two peg portions, a bridge portion, and at least one securing element, wherein the peg portions are formed by sheet material and the bridge portion is formed by sheet material, wherein the peg portions and the bridge portion are assembled or in situ assemblable to form a substantially rigid peg and bridge member, in which the bridge portion extends between the peg portions, and wherein the securing element comprises a material having thermoplastic properties,
    preliminarily stabilizing the bone portions in a desired position relative to each other,
    preparing the bone portions for implantation,
    positioning the peg and bridge member relative to the bone portions such that the bridge portion bridges a gap separating the at least two bone portions, wherein the bridge portion is positioned in bone tissue, and such that at least one peg portion extends into bone tissue of each one of the bone portions,
    positioning the securing element relative to the peg and bridge member,
    securing the positioned peg and bridge member by applying energy to the securing element for a time sufficient to liquefy at least part of the material having thermoplastic properties and making it to penetrate into the bone tissue and by letting the liquefied material re-solidify in the bone tissue to constitute a positive fit connection between the bone tissue and the securing element, and
    releasing the preliminary stabilization of the bone portions.

2. The method according to claim 1, wherein the peg and bridge member comprises at least one securing structure cooperating with the securing element and wherein the step of positioning the at least one securing element comprises positioning the at least one securing element relative to the securing structure.

3. The method according to claim 1, wherein the peg portions consist of a metal sheet.

4. The method according to claim 1, wherein the bridge portion is positioned in bone tissue with a proximal edge of said bridge portion substantially flush with a bone surface.

5. The method according to claim 1, wherein the step of preparing the bone portions comprises at least one of providing an opening in at least one of the bone portions for accommodation of the securing element, providing openings for accommodation of the peg portions, or providing a groove extending from one bone portion to another bone portion for accommodation of the bridge portion.

6. The method according to claim 1, wherein the step of positioning the peg and bridge member comprises impacting the peg portions and the bridge portion into the bone tissue of the bone portions.

7. The method according to claim 1, wherein the step of securing comprises applying vibrational energy to the securing element and liquefying the material having thermoplastic properties by pressing it against the bone tissue or against a counter element.

8. The method according to claim 1, wherein the steps of positioning and securing the peg and bridge member further comprises assembling the peg and bridge member by positioning and locking the peg portions and the bridge portion relative to each other.

9. The method according to claim 1, wherein the gap separating the at least two bone portions is an osteotomy cut, a fracture or a gap between articulating bone portions.

10. An implant for stabilizing at least two bone portions relative to each other in a human or animal patient, the implant comprising at least two peg portions, a bridge portion, and a securing element, wherein the peg portions are formed by sheet material and the bridge portion is formed by sheet material, wherein the at least two peg portions and the bridge portion are assembled or in situ assemblable to form a substantially rigid peg and bridge member, in which the bridge portion is arranged between the peg portions, wherein the bridge portion is oriented relative to the peg portions to extend into the bone tissue, wherein the securing element comprises a material having thermoplastic properties, wherein the bridge portion is configured to bridge a gap separating the at least two bone portions, wherein at least one peg portion of the at least two peg portions is configured to extend into bone tissue of a first bone portion of the at least two bone portions and at least another peg portion of the at least two peg portions is configured to extend into a second bone portion of the at least two bone portions, and wherein peg portions formed by the sheet material have an open configuration.

11. The implant according to claim 10, wherein the peg and bridge member comprises at least one securing structure cooperating with the securing element.

12. The implant according to claim 11, wherein the securing structure is at least one of a through opening in a portion of the peg and bridge member to be oriented parallel to a bone surface, a through opening in a portion of the peg and bridge member to extend into the bone tissue, or a notch in a proximal edge of the peg and bridge member.

13. The implant according to claim 10, wherein the peg portions consist of a metal sheet.

14. The implant according to claim 10, wherein the peg portions and the bridge portion are configured in a manner that the peg portions extend deeper into the bone tissue than does the bridge portion.

15. The implant according to claim 10, wherein the at least two peg portions and the bridge portion are assembled to form a substantially rigid peg and bridge member by being made of a single piece of sheet material.

16. The implant according to claim 10, wherein the peg and bridge member comprises a retention structure located on a sheet material piece oriented to extend into the bone tissue.

17. The implant according to claim 16, wherein the retention structure is at least one of a through retention opening, an indented edge or a tooth.

18. The implant according to claim 10, wherein the peg and bridge member comprises a stiffening structure.

19. The implant according to claim 18, wherein the stiffening structure is at least one of a deformed edge, a bulge, a folded edge, a folded ridge or a twist.

20. The implant according to claim 18, wherein the stiffening structure is provided in the bridge portion, which is oriented to extend on a bone surface, or on the peg portions.

21. The implant according to claim 10, wherein the peg and bridge member has a U-shaped profile.

* * * * *